United States Patent

Liu

[11] Patent Number: 4,692,551

[45] Date of Patent: Sep. 8, 1987

[54] PREPARATION OF CARBOXYPROPYLATED NON-IONIC SURFACTANTS

[75] Inventor: Kou-Chang Liu, Wayne, N.J.

[73] Assignee: GAF Corporation, Wayne, N.J.

[21] Appl. No.: 887,298

[22] Filed: Jul. 23, 1986

[51] Int. Cl.$^4$ .............................................. C07C 59/48
[52] U.S. Cl. ................................... 562/471; 562/470; 562/587
[58] Field of Search ....................... 562/587, 470, 471

[56] References Cited

U.S. PATENT DOCUMENTS

| | | | |
|---|---|---|---|
| 2,210,874 | 8/1940 | Balle et al. | 562/471 |
| 2,449,991 | 9/1942 | Gresham | 562/471 |
| 4,223,163 | 9/1980 | Guilloty | 562/587 |

*Primary Examiner*—Paul J. Killos
*Attorney, Agent, or Firm*—Marilyn J. Maue; Joshua J. Ward

[57] ABSTRACT

The process involving the reaction of an alcohol ether, $RY(OCH_2CH_2)_n$—OH, with a metal hydroxide, MOH, to produce the corresponding intermediate salt $RY(OCH_2CH_2)_nOM$ and reacting said salt with a butyrolactone,

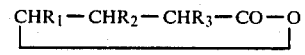

to produce the corresponding carboxypropylated product

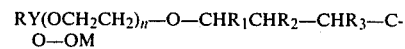

wherein R is a saturated or olefinically unsaturated aliphatic radical having from 4 to 50 carbon atoms; Y is a direct bond or phenyl optionally substituted with halogen, trihalomethyl, cyano, nitro, $C_{1-4}$ alkyl or $C_{1-4}$ alkoxy; $R_1$, $R_2$ and $R_3$ are each independently hydrogen or $C_{1-4}$ alkyl; M is a sodium, potassium or lithium cation and n is an integer having a value of from 2 to 50.

15 Claims, No Drawings

PREPARATION OF CARBOXYPROPYLATED NON-IONIC SURFACTANTS

BACKGROUND OF THE INVENTION

Prior processes have prepared carboxy alkylated surfactants by reacting 1 mole of a high molecular weight alcohol ether with 2 moles of inorganic hydroxide in flake form followed by the addition of chloroacetic acid, a known skin irritant, to produce the corresponding non-ionic surfactant. However, this process generates eye and skin irritating alkali metal chloride by-product which is difficult and expensive to separate from the desired product. Also the process requires a 1 mole excess of hydroxide reactant which is consumed in the reaction to form waste by-product metal chloride. Accordingly, the process makes inefficient use of the hydroxide to achieve alkylated surfactant and time consuming purification steps must be employed where the product is to be used as a surfactant in cosmetic or medicinal formulations.

Accordingly, it is an object of the present process to eliminate these defficiencies while providing an economical and commercially feasible process.

Another object is to provide a process for the preparation of a carboxypropylated surfactant in a high state of purity and in yields above 85%.

Still another object is to provide a process which eliminates the use of the chloroacetic acid irritant and which produces a non-ionic carboxypropylated surfactant which can be directly incorporated into a cosmetic or medicinal formulation.

Still another object is to provide a process in which the chain length of the surfactant molecule can be extended and regulated by proper selection of adduct coreactant.

THE INVENTION

According to this invention there is provided a process for preparing, in a high state of purity, a carboxyalkylated non-ionic surfactant having the formula

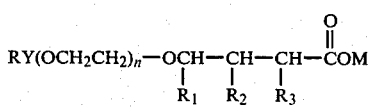    A.

wherein n has an average value of from 2 to 50, preferably 3 to 20; R is a saturated or olefinically unsaturated aliphatic radical having from 4 to 50 carbon atoms, preferably from 5 to 20 carbon atoms; Y is a direct bond or an aryl group, preferably a phenyl group, which can be optionally substituted with halogen, trihalomethyl, such as trifluoromethyl, cyano, nitro, $C_{1-4}$ alkyl or $C_{1-4}$ alkoxy; $R_1$, $R_2$ and $R_3$ are each independently selected from the group of hydrogen, or $C_{1-4}$ alkyl and M is a cation such as $Na^+$, $K^+$ or $Li^+$.

These surfactants are produced by the novel process of this invention which involves the reaction of a metal hydroxide, such as sodium, potassium or lithium hydroxide, with an alcohol ether having the formula $$RY(OCH_2CH_2)_nOH \qquad \text{B.}$$

to produce a corresponding intermediate salt having the formula $$RY(OCH_2CH_2)_nOM \qquad \text{C.}$$

The water generated during the hydroxide condensation reaction can be removed, e.g. by venting to the atmosphere, or the water of reaction can be allowed to remain in the system and be recovered with the final product, as a carrier therefor, suitable for direct incorporation into detergent and cosmetic formulations. The intermediate salt formed by the condensation reaction is then reacted with a butyrolactone having the formula

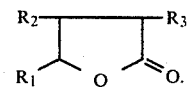    D.

In the above formulae B, C and D, the components R, Y, M, $R_1$, $R_2$, $R_3$ and n have the same definitions as set forth above in formula A. The above reaction can be summarized by the equation:

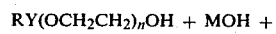

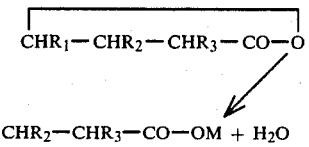

The above reactions can be carried out in the presence or absence of an inert solvent such as for example, N-methyl pyrrolidone, chlorobenzene, toluene, xylene, cyclohexane, tetrahydrofuran, or an excess of the butyrolactone reactant. The concentration of solvent, when used is not critical. For example 20–40% by weight of the active components in the reaction may be used. While the alcohol ether, inorganic hydroxide and butyrolactone can be intermixed and reacted in a one stage operation, the synthesis can also be carried out in two stages, namely by reacting the alcohol ether with the inorganic hydroxide in a first stage and then reacting the resulting ether salt with the butyrolactone in a second stage of the process to produce the surfactant of the present invention. For economic considerations, the mole ratio of alcohol ether to hydroxide fed to the reaction zone should be close to stoichiometry.

It will become apparent that the molecular weight of the surfactant molecule can be regulated by selection of the alcohol ether and/or butyrolactone reactants, which coreactant can have as many as 16, and as few as 4, carbon atoms in the molecule.

In general the above reactions are carried out at temperatures between about 25° and about 235° C. under atmospheric pressure for a period of from about 0.1 to about 50 hours; although it should be pointed out that higher reaction temperatures, for example up to 300° C. under superatmospheric pressure e.g. about 70 psig, can be employed when desired. For optimum results, it is recommended that the reaction be carried out with agitation and preferably at a temperature between about 50° and about 200° C. under atmospheric pressure for a period of from about 1 to about 20 hours.

Since the components of the present reaction are non-corrosive, acid resistant equipment is not required and since only a stoichiometric proportion of the alcohol ether and inorganic hydroxide need be employed the product can be obtained in yields greater than about 90%.

Among the alcohol ethers illustrating the primary reactant of the present invention, there is mentioned straight chain or branched chain species of butyl, amyl, hexyl, heptyl, octyl, nonyl, decyl, dodecyl, tetradecyl, octadecyl, butenyl, pentenyl, octenyl, decenyl, stearyl, eicosyl, angelyl, oleyl, erucyl, nervonyl, geranyl, linoleyl, dihydrogeranyl, palmityl, tallow, dodecenyl, tridecenyl, hexylphenyl, octylphenyl, nonylphenyl, dodecylphenyl, octadecylphenyl, tetradecylphenyl, nonadecylphenyl, nonylchlorophenyl, nonyl-trifluoromethyl-phenyl, nonyl-butoxyphenyl, octyl-cyanophenyl, tetradecyl-nitrophenyl, decyl-chloro-nitro-phenyl, nonyl-cyano-phenyl, decyl-phenyl, hexyl-napthyl and octyl-trichloronaphthyl alcohol ethers and intermixtures of alcohol ethers within the scope of this invention as hereinabove defined. The unsaturated alcohol ether reactants of this invention provide products of formula A which represent a distinctive subclass in that these surfactants have a lower melting point and a higher cloud point than their saturated counterparts. Also, because of their higher polarity, they are more soluble in water.

Representative of the butyrolactones included within the scope of this invention are butyrolactone, methyl butyrolactone, dimethyl butyrolactone, ethyl butyrolactone, tributyl butyrolactone, diethyl butyrolactone and triethyl butyrolactone.

Having thus described the invention, reference is now had to the following examples which are not to be construed as limiting to the scope of the invention described herein and as set forth in the appended claims. All ratios and amounts reported in the following examples are by weight unless otherwise indicated.

EXAMPLE I

Into a 1 liter three necked round bottom flask equipped with a thermometer, a mechanical stirrer and a vacuum line was introduced 517.5 g. (1.55 moles) of Emulphogene DA-530 (a decyl alcohol containing an average of four ethylene oxide units and 61.2 g. (1.53 moles) of sodium hydroxide. The mixture was then heated to 110° C. to dissolve the sodium hydroxide. To this solution, 131.7 g. of n-butyrolactone (1.53 moles) was added and the reaction temperature was held at 110°-115° C. for 2 hours. The corresponding carboxypropylated Emulphogene DA-530 was formed in 93.5% yield.

EXAMPLE II

Into a 1 liter three necked round bottom flask equipped as set forth in Example I was introduced 374 g. (0.65 mole) of oleyl alcohol containing an average of seven ethylene oxide units and 26 g. (0.65 mole) of sodium hydroxide. The mixture was heated at 110° C. for 1.5 hours to form the corresponding sodium alkoxide salt and water. The water generated was removed under reduced pressure, after which 55.9 g. (0.65 mole) of n-butyrolactone was added. The resulting liquid was heated at 100°-110° C. for 2 hours and the corresponding carboxypropylated nonionic compound was obtained in 95.5% yield.

EXAMPLE III

Into a 1 liter three neck round bottom flask equipped as in Example I was introduced 344 g. (1.01 moles) of tridecyl alcohol containing an average of three ethylene oxide units and 40.25 g. (1.01 moles) of sodium hydroxide. The mixture was heated to 115° C. and the water generated was removed from the system under reduced pressure. After the removal of water, 86.6 g. (1.01 moles) of n-butyrolactone was added and the solution was heated at a 100° C. for 2 hours. The corresponding carboxypropylated product was recovered in 94.8% yield.

Properties of the products of Examples I, II and III are presented in the following Table.

TABLE

|  | I | II | III |
| --- | --- | --- | --- |
| Draves Wetting Test ASTM-D2281-60A (Seconds) | 14 | 177 | 21 |
| Surface Tension (dynes/cm) | 26.8 | 32.2 | 26.6 |
| Lime soap dispersion % | 10 | 10 |  |

EXAMPLE IV

To a 1 liter three necked round bottom flask equipped as set forth in Example I was introduced 681 g. (1.01 moles) of Igepal-CA-630 (an octyl phenol containing an average of ten ethylene oxide units) and 56.7 g. (1.01 moles) of potassium hydroxide. The mixture was heated at 115° C. for 2 hours to form the corresponding potassium alkoxide salts and water reaction. The water which was generated was removed under reduced pressure and 87 g. (1.01 moles) of n-butyrolactone was added. The resulting liquid was heated at 110°-115° C. for 2 hours after which the corresponding carboxypropylated compound was obtained in 95.5% yield.

What is claimed is:

1. The process which comprises reacting an alcohol ether having the formula

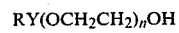

RY(OCH$_2$CH$_2$)$_n$OH with a metal hydroxide having the formula MOH, to produce the corresponding salt having the formula

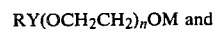

RY(OCH$_2$CH$_2$)$_n$OM and reacting said salt with a butyrolactone having the formula

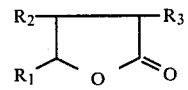

at a temperature of between about 50 and about 300° C., under a pressure of from about 14 to about 70 psig. until the desired conversion has taken place to produce the corresponding carboxypropylated polyethylene glycol salt having the formula

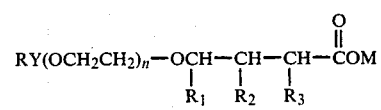

wherein n has an average value of 2 to 50; R is a saturated or olefinically unsaturated aliphatic radical having from 4 to 50 carbon atoms; Y is a direct bond or an aryl group optionally substituted with a member selected from the group consisting of halogen, trihalomethyl, cyano, nitro, alkyl and alkoxy; $R_1$, $R_2$ and $R_3$ are each independently hydrogen or alkyl having from 1 to 4 carbon atoms and M is a cation selected from the group consisting of $Na^+$, $K^+$ and $Li^+$.

2. The process of claim 1 wherein the process is carried out in two stages and wherein the reaction of the alcohol ether and a metal hydroxide to produce a salt represents the first stage and the reaction of said salt and said butyrolactone represents the second stage and wherein both reactions are carried out at a temperature of between about 50° C. and about 235° C.

3. The process of claim 1 wherein the process is carried out in a single stage and the alcohol ether, metal hydroxide and butyrolactone are intermixed in the reaction zone.

4. The process of claim 1 wherein the mole ratio of alcohol ether to metal hydroxide is about 1:1.

5. The process of claim 1 wherein water is generated in the reaction between the alcohol ether and the metal hydroxide and the water of reaction is recovered with the product.

6. The process of claim 1 wherein water is generated in the reaction between the alcohol ether and the metal hydroxide and the water of reaction is removed prior to the addition of the butyrolactone.

7. The process of claim 1 wherein the reaction is carried out in the presence of an inert solvent.

8. The process of claim 7 wherein said solvent is selected from the group consisting of toluene, xylene, cyclohexane, butyrolactone, N-methyl pyrrolidone, chlorobenzene, tetrahydrofuran and mixtures thereof.

9. The process of claim 8 wherein the solvent is n-butyrolactone.

10. The process of claim 1 wherein the hydroxide is sodium hydroxide.

11. The process of claim 1 wherein the hydroxide is potassium hydroxide.

12. The process of claim 1 wherein said alcohol ether is decyl alcohol containing an average of four ethylene oxide units.

13. The process of claim 1 wherein said alcohol ether is oleyl alcohol containing an average of seven ethylene oxide units.

14. The process of claim 1 wherein said alcohol ether is tridecyl alcohol containing an average of three ethylene oxide units.

15. The process of claim 1 wherein said alcohol ether is octylphenol containing an average of ten ethylene oxide units.

* * * * *